United States Patent [19]
Ryan
[11] Plant 4,779
[45] Oct. 20, 1981

[54] IMPATIENS PLANT NAMED CHINOOK

[76] Inventor: John J. Ryan, 39877 Sundale Dr., Fremont, Calif. 94538

[21] Appl. No.: 150,699

[22] Filed: May 16, 1980

[51] Int. Cl.³ ..... A01H 5/00
[52] U.S. Cl. ..... Plt./68
[58] Field of Search ..... Plt./68

*Primary Examiner*—Robert E. Bagwill
*Attorney, Agent, or Firm*—James R. Cypher

[57] ABSTRACT

This invention relates to a new and distinct variety of New Guinea Impatiens plant, known by the cultivar name Chinook, a seedling resulting from the cross pollenation of unpatented pollen parent 76-73-1 and unpatented pistil parent 76-201-1 and is distinguished by its spreading growth habit; many small, slightly cupped, lightly candy-striped red-purple flowers; and very dark, reddish green, metallic looking (black-green with a dull shine) non-variegated foliage.

1 Drawing Figure

BACKGROUND OF THE INVENTION

The present new variety (seedling) was discovered by me in a commercial greenhouse in Fremont, Calif., as a result of a definite breeding program to produce improved and different commercial varieties of plants.

The cross pollenation of unpatented pistil parent 76-201-1 and the unpatented pollen parent 76-73-1 produced the distinct new variety herein described and selected for propagation by cuttings. Repeated propagations and flowerings of my new variety through asexual reproduction by terminal or stem cuttings grown in pots in a plastic (polyethylene) greenhouse in Fremont, Calif., under normal environmental conditions show that the characteristics described come true to form and are established and transmitted through succeeding generations.

BRIEF SUMMARY

The known commercial variety to which Chinook would be closest in characteristics is Aztec, U.S. Plant Pat. No. 4,193, granted Jan. 17, 1978. Chinook is much like Aztec in growth habit (spreading) and flower form (Many small, slightly cupped) but distinctly different in the following ways:

1. The foliage of Aztec is variegated whereas the foliage of Chinook is not variegated under greenhouse growing conditions,
2. The color of the foliage is very dark reddish-green and can be described as looking almost metallic (black-green with a dull shine),
3. The flower of Aztec is not candy striped, whereas the flower of Chinook is lightly candy striped,
4. The flower color is red-purple and could be described as red-plum in color,
5. A spreading growth habit, but Chinook has shorter internodes than Aztec.

DESCRIPTION OF THE PHOTOGRAPH

This new variety of Impatiens plant is illustrated by the accompanying photograph which is a close-up view of the foliage and flowers and illustrates the color of the flowers as nearly true as is reasonably possible to obtain by conventional photographic procedures.

DETAILED DESCRIPTION

Referring to the botanical details of my new variety, the following detailed description is based on observations made on Mar. 10, 1980. All plants were grown under normal environmental conditions in greenhouses. Color readings were taken during daylight hours in full sun, and all colors are based on the Royal Horticultural Society Colour Chart.

I. PLANT

Name: Chinook
Origin: Seedling of the cross-pollenation of the unpatented pistil parent 76-201-1 and the unpatented pollen parent 76-73-1.
Form: Spreading.
Height to flowering: 20 cm to 25 cm.
Growth: Fast.
Type of cutting: Terminal or stem.
Rooting time: Typical, 10–14 days.
Rooting habit: Fast, dendritic.

II. FOLIAGE

Arrangement: Lower leaves of any break opposite (usually one set); upper foliage of any break whorls of 3 to 7 (any over 4 seem to be two nodes compressed).
Shape: Elliptical to lanceolate—many asymmetric.
Tip: Acuminate.
Base: Attenuate.
Margin: Serrulate.
Veination: Pinnate.
Size: Length of blade and petiole 8.5 cm to 12.5 cm; length of blade 5.5 cm to 9.0 cm; width of blade at widest point 2.0 cm to 3.0 cm.
Surface: Glabrous.
Variegation: None under our conditions.
Color:
1. *Petiole.*—a. Upper 53A-53B; b. Lower 46A.
2. *Veins.*—a. Upper 53A-53B; b. Lower 46A.
3. *Leaf.*—a. Upper 137A with a thin red overlay of 53B; b. Lower 183B.

III. STEM

Color: 185A on side facing sun and especially colored just above node.
Internode:
1. *Length.*—Short to average.
2. *Size.*—Less than average as with Aztec, and even shorter than Aztec.

Node expanded (relative to internode): Slight to none.

Breaking action: Good to excellent.

IV. FLOWER

Form: Typical, but slightly cupped as with Aztec and Pawnee.

Borne: End of branches, terminal.

Blooming habit:

1. *Relative number.*—Many.
2. *Time to flowering.*—Short.
3. *Longevity.*—3 to 5 days.

Size of mature flower: First flower on a plant may be small.

| | | |
|---|---|---|
| 1. | *Length.*—5.0 cm. | Varies little, |
| 2. | *Width.*—5.0 cm. | |
| 3. | *Spur.*—5.5 cm. | slightly cupped |

Color: Lightens under high light-moving towards red, and losing blue pigment.

| | | |
|---|---|---|
| 1. | *Eye.*—68A fading to 57C to 57D. | |
| 2. | *Middle* | 57A |
| 3. | *Edge* | |

-continued

| | |
|---|---|
| 4. | *Pedicel.*—150C (on top in sun 46A to 46B). |
| 5. | *Candy-stripe.*—45A. |

V. REPRODUCTIVE ORGANS

Stamen:

| | | |
|---|---|---|
| 1. | *Anthers* | Typical, fused hood (57B) over |
| 2. | *Filaments* | pistil. |
| 3. | *Pollen.*—a. Color—158B to 158C; b. Abundance—plenty. | |

Pistils:

| | | |
|---|---|---|
| 1. | *Style* | Typical but colored 187A. |
| 2. | *Ovaries* | |

I claim:

1. A new and distinct form of Impatiens plant as described and illustrated, known by the cultivar name Chinook.

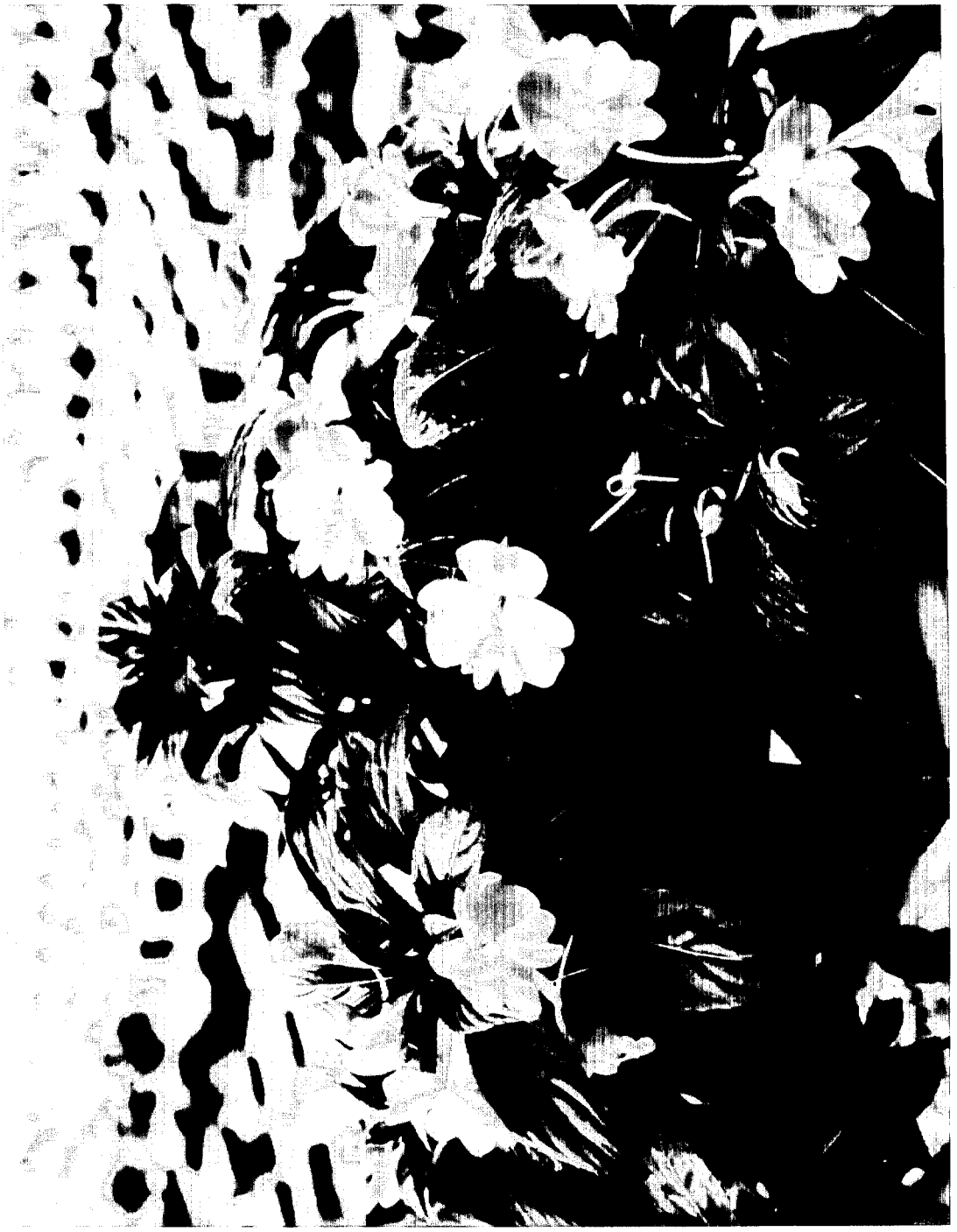

* * * * *